United States Patent [19]

Miraki

[11] Patent Number: 5,549,554

[45] Date of Patent: Aug. 27, 1996

[54] CATHETERS HAVING SEPARABLE REUSABLE COMPONENTS

[75] Inventor: Manouchehr Miraki, Aliso Viejo, Calif.

[73] Assignee: Advanced Cardiovascular Systems, Inc., Santa Clara, Calif.

[21] Appl. No.: 382,768

[22] Filed: Feb. 2, 1995

Related U.S. Application Data

[63] Continuation-in-part of Ser. No. 222,145, Apr. 1, 1994, and Ser. No. 265,602, Jun. 24, 1994.

[51] Int. Cl.⁶ ............................................. A61M 29/00
[52] U.S. Cl. ........................... 604/101; 604/283; 604/284; 604/53
[58] Field of Search ........................... 604/94, 96, 101, 604/167, 283, 284, 05, 161, 165; 606/192, 195, 196, 194, 199

[56] References Cited

U.S. PATENT DOCUMENTS

| | | | |
|---|---|---|---|
| 3,516,408 | 6/1970 | Montani | 604/101 |
| 3,937,224 | 2/1976 | Uecker | 128/348 |
| 4,425,124 | 1/1984 | Womack | 604/283 |
| 4,769,017 | 9/1988 | Fath | 604/283 |
| 4,834,710 | 5/1989 | Fleck | 604/171 |
| 4,840,690 | 6/1989 | Melinyshyn | 604/101 |
| 4,902,273 | 2/1990 | Choy | 604/101 |
| 5,203,771 | 4/1993 | Melker | 604/283 |
| 5,217,439 | 6/1993 | McClusky | 604/275 |
| 5,234,411 | 8/1993 | Vaillancourt | 604/171 |
| 5,348,542 | 9/1994 | Ellis | 604/283 |

FOREIGN PATENT DOCUMENTS

| | | |
|---|---|---|
| 0274129 | 7/1988 | European Pat. Off. . |
| 0339093 | 11/1989 | European Pat. Off. . |
| WO93/13827 | 7/1993 | WIPO . |
| WO93/20882 | 10/1993 | WIPO . |

*Primary Examiner*—Randall L. Green
*Assistant Examiner*—Ceralin Smith
*Attorney, Agent, or Firm*—Crosby, Heafey, Roach & May

[57] ABSTRACT

Dual headed catheter assemblies are provided with a tubular central instrument body portion connected at each end to an elongate tubular distal body, each of which may be provided with an expansible balloon for dilatation purposes. One or more releasable connectors may be provided for sealingly connecting each of the tubular distal bodies to the central instrument body portion to allow for replacement of the tubular distal body and to simplify potential resterilization and reuse of the central instrument body portion. Alternative embodiments include multiple inflation lumens each provided with an individual inflation port which may be preferentially accessed by a fluid conducting inflation assembly configured to preferentially access individual inflation ports. The dual headed catheter with replaceable components may be utilized in place of multiple single headed catheters to perform medical procedures involving repeat access to vascular target sites.

32 Claims, 4 Drawing Sheets

CATHETERS HAVING SEPARABLE REUSABLE COMPONENTS

RELATED APPLICATIONS

The present invention is a continuation-in-part of two earlier filed co-pending applications, Ser. No. 08/222,145, filed Apr. 1, 1994, and Ser. No. 08/265,602, filed Jun. 24, 1994.

FIELD OF THE INVENTION

The present invention relates in general to the field of medical catheters and, more particularly, to catheters having two functional assemblies on opposite ends of a central catheter instrument. The catheters of the present invention further incorporate separable components that can be reused if desired.

BACKGROUND OF THE INVENTION

Over the years, medical catheters have been developed and refined to provide useful devices for the diagnosis and treatment of disease without invasive surgery. As a result, medical catheters are widely used for a variety of modern, less invasive medical procedures. Unfortunately, the vast majority of catheters available today are manufactured and packaged as disposable, single use devices. While these conventional catheters are undeniably beneficial in shortening hospital stays and in reducing complications associated with surgery, the precision and quality control required to fabricate these instruments makes them expensive to produce and use. This is particularly true for disposable catheters. Moreover, the use of disposable catheters tends to increase the amount of medical and packaging waste generated while eliminating the ability of the user to adapt the configuration of the catheter to specific needs and operating conditions.

These and other limitations associated with the use of disposable catheters are particularly well illustrated by catheters used for the treatment of vascular diseases. Over the last decade a medical procedure known as angioplasty has become widely accepted as a safe and effective method for opening stenoses throughout the vascular system and particularly for opening stenoses in the coronary arteries. The most common form of angioplasty practiced to date is known as percutaneous transluminal coronary angioplasty (PTCA).

In virtually all forms of PTCA, a long, hollow dilatation catheter having an inflatable balloon at its distal end is guided into a patient's artery and, using a fluoroscope and radiopaque markers for visualization, maneuvered within the artery until the balloon is positioned across the narrowing stenosis responsible for inadequate blood flow to the heart. Generally, a thin guide wire is first advanced into position and used to maneuver and direct the catheter. Once positioned, the balloon is inflated for a brief period by supplying pressurized fluid to the balloon through an inflation lumen in the catheter body, to displace the plaque or other obstructions causing narrowing in the artery. Applying negative pressure to the inflation lumen collapses the balloon allowing the catheter to be withdrawn when the stenosis has been opened and blood is once again flowing adequately. Thus, in contrast to the serious risks and complications previously associated with open-heart surgery, PTCA can be utilized to open blocked coronary arteries using only a small vascular incision through which the dilatation catheter is inserted and operated.

Several different types of entirely disposable dilatation catheters are currently in use and may be generally classified based upon their interaction with the guide wire. One common dilatation catheter design is known as the "fixed-wire" or integrated "balloon-on-a-wire" dilatation catheter. These single-lumen catheters utilize a relatively small diameter guide wire positioned within the inflation lumen and fixed to the distal end of the dilatation balloon. This design produces a very small diameter or "low-profile" assembly which is able to cross severely narrowed lesions and to navigate tortuous vascular pathways. More recent balloon-on-a-wire designs allow the catheter to be removed while leaving the guide wire in place across the stenosis.

Another common type of dilatation catheter design is known as the "over-the-wire" balloon catheter. This device typically utilizes a relatively large lumen for passage of a removable guide wire and for injection of angiographic visualization dye to assist in the placement of the distal expansible balloon across a target lesion. A second, parallel lumen is provided for inflation and deflation of the balloon with such a design commonly referred to as a "dual lumen" catheter. Alternatively, a "coaxial" design may be utilized where the catheter body defines an annular inflation lumen around the internal guide wire lumen.

More recently, "rapid exchange" catheters have been developed to allow for the quick removal and replacement of the catheter from the patient while leaving the guide wire in place for rapid reaccess to the target lesion. One such rapid exchange system utilizes a conventional inflation lumen and a relatively short guiding or through lumen at the distal end of the catheter to slidably receive the guide wire. The distal guide wire portion is permanently fused to the catheter body tube which is formed of a flexible material that allows the catheter to be pushed and advanced through curved vascular pathways.

Other "rapid exchange" catheter designs use a dedicated guide wire lumen provided with a longitudinal split seam. These designs enable the operating physician to remove the catheter by simply grasping the exposed proximal end of the implanted catheter and pulling the catheter tube off of the guide wire as it is removed while leaving the guide wire in place. Still other designs use a blade to split the catheter from the guide wire upon removal of the catheter from the patient. For example a sharpened blade may be mounted within the central bore of the catheter proximal Y-connector to slit the catheter and separate it from the guide wire as the catheter is extracted.

While these disposable catheter designs have proven effective under a variety of conditions, their disposability and specific functionality limit the capacity of the surgeon to adapt to changing or unexpected situations. This drives up the costs associated with their use as several alternative catheters may be necessary to accomplish a simple procedure. For example, it is often necessary to exchange entire catheters during angioplasty procedures. The catheter exchange may be required for any one of several reasons including catheter balloon malfunction, the inability of the specific balloon size to adequately dilate the vascular stenoses, or the need to insert an additional device to remove vascular material. In each of these situations, the original dilatation catheter must be removed and a new catheter inserted. It is estimated that about half of the angioplasty procedures require the use of more than one dilatation catheter. Presently, all of the catheters used during such procedures are discarded after a single use.

The disposal of these technically advanced, precision manufactured instruments which are otherwise suitable for repeat use reduces the efficiency of the entire procedure. Similarly, the use of two or more dilatation catheters in a single operation significantly increases the costs to both the patient and the medical provider as the patient must pay for the cost of an additional dilatation catheter which may be on the order of several hundreds of dollars. Further, due to the increased demand for alternative and replacement catheters, the medical provider must stock a larger inventory of catheters which requires more storage space and packaging. This also increases the amount of waste or recyclable matter associated with the use of multiple, non-reusable catheters during a single operation, further increasing the administrative burdens and associated expenses.

One early effort at overcoming the disadvantages associated with completely disposable catheters involved their resterilization and reuse. However, this proved to be unworkable in practice. Most of the currently available catheter designs are fabricated as substantially integral devices having the majority of components joined or fused together using permanent connections. Such configurations preclude the efficient resterilization of the apparatus. For example, many standard catheter designs incorporate a closed system inflation lumen that must be entirely purged prior to sterilization to ensure the effectiveness of the procedure. Complete purging of the system after use is labor intensive, time consuming and expensive, if possible at all. Moreover, in order to reuse the catheter several delicate pieces of the catheter assembly, including the fragile dilatation balloons, must be repeatedly subjected to harsh sterilization conditions which may increase the possibility of material deterioration and subsequent balloon malfunction.

An alternative solution to the problems associated with single use catheters may be found in copending U.S. patent application Ser. No. 08/265,602 which is directed to catheters incorporating separable components that may be reused or disposed of, as desired. Typically, these catheter designs incorporate a rugged, reusable proximal end portion combined with a disposable distal end portion fabricated from reliable, yet cost effective materials. The proximal ends of the catheters are designed to facilitate their cleaning and resterilization. As a result, components of these catheters may be resterilized and reused which results in substantially reduced costs. Although these reusable catheters are a significant improvement over prior art disposable catheters and allow for the economical use of alternative balloon sizes and configurations during surgery, precious surgical time may be required to change or replace the disposable distal ends. This substitution may be complicated further by the hectic environment of the operating room where the apparatus may be wet, slippery, and difficult to see or manipulate.

Accordingly, it is an object of the present invention to provide catheter designs which incorporate resterilizable and reusable components.

It is another object of the present invention to provide catheter designs having two operational ends that can be rapidly substituted for one another.

It is still another object of the present invention to provide dilatation catheters which allow for the uncomplicated substitution or modification of components and catheter configurations.

It is yet another object of the present invention to provide dilatation catheters which require less storage space than conventional catheters while simultaneously reducing the amount of packaging necessary to maintain their sterility prior to use.

SUMMARY OF THE INVENTION

These and other objects are achieved by the double or dual-headed balloon catheter assemblies of the present invention which, in accordance with broad structural aspects thereof, comprise a generally elongate tubular body having first and second distal ends coupled to a central instrument portion. The assemblies may be configured to any popular catheter design including fixed wire, balloon-on-a-wire, over-the-wire, rapid exchange, single and multi-lumen designs as known in the art. Preferably, the first and second distal ends further include first and second dilatation balloons or other instruments, one provided at each respective distal end.

The elongate catheter body further includes a first fluid delivery mechanism such as an inflation port provided in the central portion of the catheter instrument body. The first delivery mechanism communicates with the first dilatation balloon and delivers an inflation media to the first balloon. The central portion of the elongate catheter body is also provided with a second fluid delivery mechanism or inflation port communicating with the second dilatation balloon for delivering an inflation media to the second balloon.

In addition, the dual-headed or double balloon catheter assemblies of the present invention further include an inflation assembly which is slidably positioned about the central portion of the elongate instrument body and adapted to be secured in fluid conducting communication with either the first fluid delivery mechanism or inflation port or the second fluid delivery mechanism or inflation port. The inflation assembly is adapted to provide inflation media from an inflation source through the first or second fluid delivery mechanism, as appropriate. A removable protective sheath may be coupled to the inflation assembly to cover the distal end that is not presently in use.

An exemplary fluid delivery mechanism includes hypotube passageways provided in the central portion of the catheter instrument body and communicating with the respective flexible catheter bodies of the distal ends and the inflation ports, with appropriate seals provided to prevent inflation media from flowing to the other flexible distal catheter body (i.e., the one not in use).

In a "rapid-exchange" embodiment of the present invention, guidewire ports are provided at each of the first and second distal ends which communicate with guidewire lumens extending through the respective distal openings at each distal end.

In an "over-the-wire" embodiment of the present invention, a guidewire lumen extends from one distal opening entirely through the elongate body to the other distal opening. The fluid delivery mechanism includes passageways provided in the central portion and communicating with the respective flexible catheter bodies of the first and second distal ends and their respective inflation ports, with adjustable seals provided to prevent inflation media from flowing to the flexible distal catheter body not in use at the time.

In a "long monorail over-the-wire" embodiment of the present invention, the operation principles of "over-the-wire" and "rapid-exchange" catheters may be interchangeably used. Two guidewire ports are provided adjacent opposite ends of the central body portion, each communicating with a guidewire lumen which extends from one distal opening through the elongate body to the other distal opening. When the guidewire extends through the guidewire port closer to the distal end being used, the catheter system operates under the principles of a "rapid-exchange" catheter. Alternatively, when the guidewire extends through the guidewire port farther away from the distal end being used, the catheter system operates under the principles of an "over-the-wire" catheter. This catheter system can be operated under either principle, and also facilitates convenient guidewire exchange while keeping the dilatation balloon positioned at the site of the stenosis.

In a "fixed-wire" embodiment of the present invention, guidewires are affixed to the central body portion and extend through each distal end. The delivery mechanism includes hypo-tube passageways provided in the central portion and communicating with the respective flexible catheter bodies of the distal ends and the inflation ports, with appropriate seals provided to prevent inflation media from flowing to the other flexible distal catheter body (i.e., the one not in use).

The principles of the present invention also relate to methods of performing angioplasty procedures to dilate stenoses located in vessels inside a patient. The methods comprise the steps of providing a catheter assembly according to the embodiments described above and elsewhere in the following detailed description of the invention. The methods further include the steps of positioning the inflation assembly over the location of the first inflation port, and then inserting the first distal end of the catheter assembly into a patient's vessel and advancing the first distal end in the vessel until the first dilatation balloon is positioned across the stenosis. Inflation media is then delivered through the first inflation port and the first delivery mechanism to inflate the first dilatation balloon.

If catheter exchange is required, the first distal end of the catheter assembly is withdrawn from the patient's vessel. In this situation, the method of the present invention then includes the steps of positioning the inflation assembly over the location of the second inflation port and inserting the second distal end of the catheter assembly into the patient's vessel and advancing the second distal end until the second dilatation balloon is positioned across the stenosis. Inflation media is then delivered through the second inflation port and the second delivery mechanism to inflate the second dilatation balloon. At the end of the procedure, the second distal end of the catheter assembly is withdrawn from the patient's vessel.

In this manner, the present invention provides two easy-to-use catheter systems on a single, lower cost catheter assembly. This allows angioplasty and catheter exchange to be performed economically, quickly, and conveniently while retaining all the desirable safeguards. Cost reduction is achieved by providing one dual function catheter assembly instead of two separate catheters, which also results in fewer disposable materials, and less inventory and lower administrative costs for the hospitals.

Further economies are achieved by providing the catheters of the present invention with a combination of disposable and reusable components. Preferably, at least one of the first and second distal ends having expansible dilatation balloons is disposable while at least the central portion of the instrument is reusable and releasably joined to the other components through a connection. The central instrument body portion, which may be selected from any one of a variety of configurations, is preferably constructed of rugged, resterilizable materials while the disposable distal end portions are preferably fabricated using reliable, but relatively inexpensive materials, specifically designed for one-time use.

In accordance with the teachings of the present invention, all types of dual-headed catheters, including diagnostic catheters, guiding catheters, dilatation catheters, over-the-wire, balloon-on-a-wire, and rapid exchange catheter configurations may be fabricated having the reusable central instrument body portion and disposable distal ends. These unique combinations further reduce the unit costs of the apparatus, simplify their fabrication, enhance their storage efficiency and decrease the amount of packaging and medical waste generated in conjunction with their use as single, reusable devices are used in place of multiple disposable devices.

Moreover, the unique modular construction of the reusable dual-headed dilatation catheters of the present invention allows different catheter components to be substituted or interchanged depending on the specific needs of the operating physician. For example, the reusable central instrument body portion may include a Y-connector, a Y-connector in conjunction with a tubular proximal body, an integrated splitter or simply the tubular proximal body of a catheter. Similarly, the size, type or configuration of the disposable instruments on the distal end portions or the expansible dilatation balloons may be altered. In addition, a variety of connections may be used to join the selected central instrument portions and distal end portions.

The reusable central portions and connectors may be fabricated of materials which are amenable to repeated sterilization through common techniques such as autoclaving, chemical exposure or radiation. Materials which are preferred for the reusable components of the catheter include glass, metal alloys such as stainless steel or Nitinol, ceramics or polymeric compounds. Further, the reusable catheter components may be configured to facilitate cleaning and sterilization by omitting small voids and other hard to clean recesses. In this regard the reusable portions may be further adapted to facilitate sterilization by the inclusion of purge valves or other mechanisms designed to improve access to their interiors.

The distal end portions of the catheters, preferably designed to be disposable, may be of variable lengths and configurations depending on the type of catheter assembly and the functions it must perform. For example, when the catheter is a rapid exchange design the central portion may be relatively long and the distal ends having the expansible balloons may be relatively short with dual lumen configurations for the insertion of guide wires. Conversely, when an integrated balloon-on-a-wire catheter is to be used, the disposable distal ends may constitute almost the entire length of the device having a relatively short central portion. In either case, the disposable distal ends are fabricated of reliable, yet cost effective disposable materials. Further, the disposable distal end of the present invention may be coded using colors, bands, alphanumeric characters or other symbols to make them readily distinguishable in an operating room environment.

The separable components of the catheter bodies may be connected at any time, including up to and during their use. The connection may be made by hand or through the use of specially designed tools depending upon the nature of the assembly and the connection configuration. While various types of releasable connections may be employed on the central instrument portions, they generally include at least one connecting member positioned on the central portion of the catheter body which is adapted to sealingly engage the first or second distal end which may optionally include a mating second connecting member. For example, a disposable distal end may be releasably attached to a reusable central body portion using various connections including compression fittings, snap connectors, single or double headed barbed connectors, luer connectors, or threaded assemblies. Moreover, each of the different connection types may be used in conjunction with each of the various catheter configurations depending upon the needs of the operating physician.

Preferably the connection is a low profile design that does not substantially increase the circumference of the catheter body. Whatever type of connection is employed, releasable connecting members are preferably configured to allow fluid conducting communication between the reusable central portion and the disposable first and second distal ends through at least one passage or lumen. This affords a reliable, fluid tight mechanism for conducting inflation media to the expansible balloons at the distal ends. Separate lumens can also be provided through connecting members for the insertion and tracking of the guide wire or for the injection of drugs or radiopaque markers.

Other objects, features and advantages of the present invention will become apparent to those skilled in the art from a consideration of the following detailed description of exemplary embodiments thereof taken in conjunction with the associated figures which will first be described briefly.

DETAILED DESCRIPTION OF THE INVENTION

While the present invention may be embodied in many different forms, disclosed herein are specific illustrative embodiments thereof that exemplify the principles of the invention. It should be emphasized that the present invention is not limited to the specific embodiments illustrated.

In particular it must be emphasized that the modular adaptability of the present invention provides for the association of a wide variety of distal ends and central instrument bodies beyond those shown. Similarly, various connections may be used with each selected catheter configuration and the choice of connection employed with any given catheter assembly is in no way limited to the exemplary embodiments illustrated. For example, as will be disclosed in detail, it is within the scope of the present invention to reverse the orientation of male and female connecting members with respect to the central portion and distal ends of the catheter assembly, connect the central portion to the distal ends using a double-male barbed connector, or to provide connecting members on either the central portion or each distal end.

Alternatively, dual headed designs having only one of the distal ends releasably connected are also contemplated as being within the scope of the present invention. Similarly, any separable take apart, multi-component configuration is contemplated as being within the scope of the present invention. While it is preferred that at least the central portion of the catheters of the present invention have the capacity for reuse, reuse is not essential to the present invention. Thus, the reusable components may be used once and disposed of or resterilized and reused.

While the present invention is particularly useful for dilatation catheters, those skilled in the art will appreciate that separable or releasably engageable bodies may be used in conjunction with all types of catheters. Accordingly, while the following discussion is primarily directed to dilatation catheters, the principles disclosed herein are applicable to a wide variety of catheters.

Common medical terms for catheter orientation will be used. Accordingly, the "distal" end of the catheter, guide wire or other element is the end farthest away from the physician who is using the device at that time while the "proximal" end is the end closest to the operating physician. Thus, with the dual headed designs of the present invention, the central portion of the apparatus functions in a manner analogous to the "proximal instrument" of a traditional, single headed device while each respective distal end functions as a conventional "distal end" when in use. Further, each portion of the device may have its own proximal instrument and distal end.

Moreover, it should be noted that each disposable distal end or body may be fitted at its own proximal instrument with a second connecting member adapted to releasably engage a reciprocal connecting member fitted on the corresponding end of the central portion. In addition to compression fittings, exemplary connections which may be used in these embodiments are threaded connectors including luer connectors, snap connectors and barbed connectors. Further, each different connection may be combined with all types of disposable distal ends including those used in dilatation catheters, over-the-wire, balloon-on-a-wire and rapid exchange catheter configurations. Finally, in these and other embodiments it is clearly within the scope of the invention to reverse the orientation of male and female connecting members with respect to the central portion and the distal ends of the catheter assembly, or connect the central portion to the distal ends using a double-male barbed connector. Similarly, when a single connecting member such as a barb is used, it is within the scope of the present invention to place it on either of the central portion or the respective distal ends.

Figure 1:
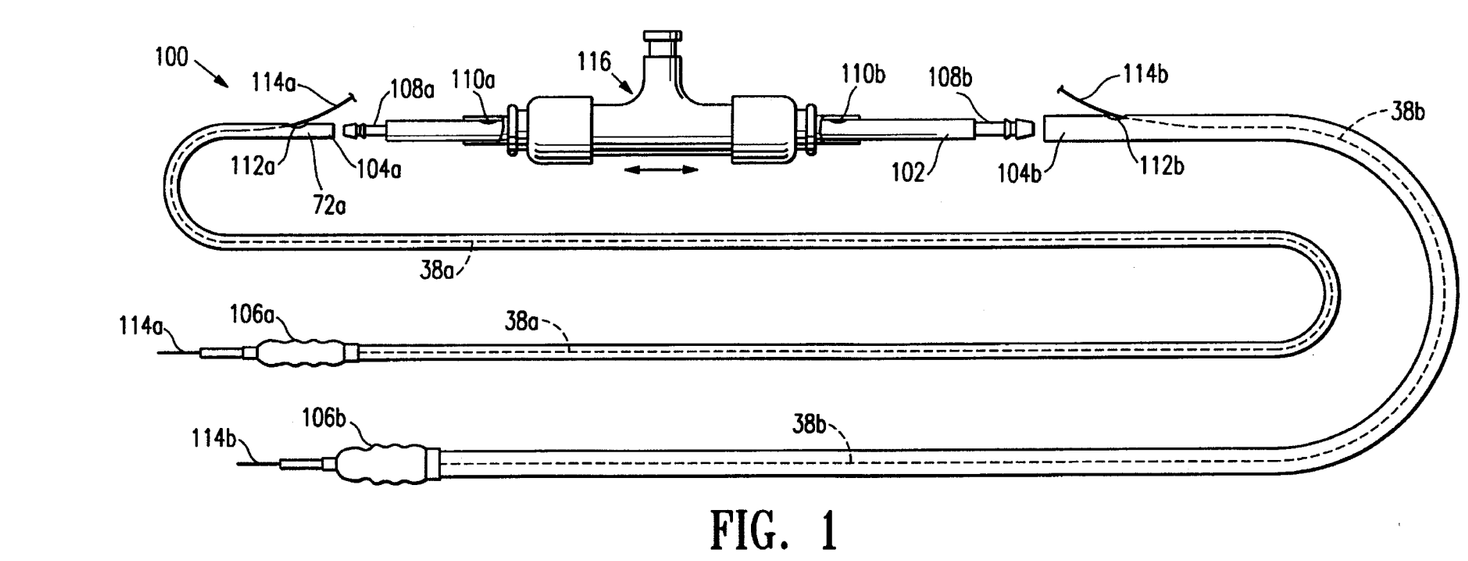
FIG. 1 is a partial fragmentary view of an exemplary catheter illustrating the principles of the present invention.

Referring now to the drawings, FIG. 1 shows an exemplary disassembled rapid exchange balloon catheter of the present invention generally denoted by the reference numeral 100. Catheter 100 includes an elongate central catheter body portion 102 having flexible distal portions and two disposable distal ends or distal bodies, a first distal body 104a and a second distal body 104b, positioned at opposite ends of central catheter body 102. A first dilatation balloon 106a is provided at the distal end of first distal body 104a, while a second dilatation balloon 106b is provided at the distal end of second distal body 104b. Central catheter body 102 further includes inflation ports 110a and 110b positioned on its surface proximal with respect to distal bodies 104a, 104b. Inflation ports 110a, 110b are initially sealed by a protective layer of material (not shown) to prevent blood or other materials from entering therethrough. This protective layer is preferably made from the same material as dilatation balloons 106a, 106b. Guidewire ports 112a, 112b are provided for insertion of guidewires 114a, 114b. A inflation assembly 116 is slidably positioned on central catheter body 102 and operates in the manner described hereinbelow.

Figure 2:
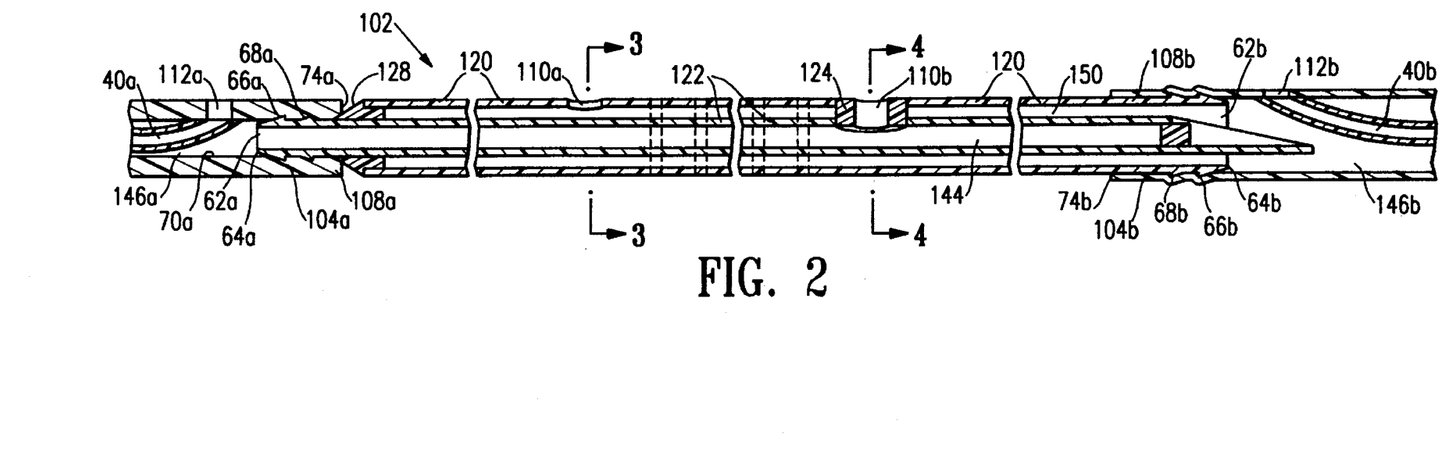
FIG. 2 is an enlarged fragmentary cross-sectional view of the central body portion of the exemplary catheter of FIG. 1.

As best illustrated in FIG. 2, in the embodiment of the present invention illustrated in FIGS. 1–4, the central or "proximal" portion of central catheter body 102 is formed of an outer hypotube 120 and an inner hypotube 122. Inner hypotube 122 is positioned axially inside outer hypotube 120, and is connected to outer hypotube 120, typically by soldering or welding 124, at the location of the inflation port 110b. One end of outer hypotube 120 is connected to inner hypotube 122 at radial connection 128 which, as is well known in the art, may be formed using adhesives, soldering, welding, laser-welding or brazing. As will be appreciated by those skilled in the art, central catheter body 102 may be fabricated using polymeric materials, biocompatible metals or metal alloys including stainless steel. For increased flexibility and kink resistance, central catheter body 102 is often formed of Nitinol, a nickel-titanium alloy. Regardless of the material used, central catheter body 102 can be coated with Teflon® to enhance its fluid conducting properties By way of example only, the embodiments of the invention shown in FIGS. 1–4 typically have an overall length of approximately 170 cm to 175 cm. Inner hypotube 122 has an inner diameter of about 0.017 inches and an outer diameter of about 0.023 inches while outer hypotube 120 has an inner diameter of about 0.034 inches and an outer diameter of about 0.040 inches. The length of central catheter body 102 is approximately 110 cm, while the length of each distal catheter body 104a and 104b is approximately 30 cm. The outer diameter of the distal catheter bodies 104a and 104b is about 2.5 French (about 0.0825 cm). Guidewires used in the rapid exchange embodiments are preferably of a standard length of 175 cm. While these exemplary embodiments apply to rapid exchange embodiments, those skilled in the art will appreciate that similar dimensions are applicable to other embodiments of the present invention.

Figures 3, 4, 5:
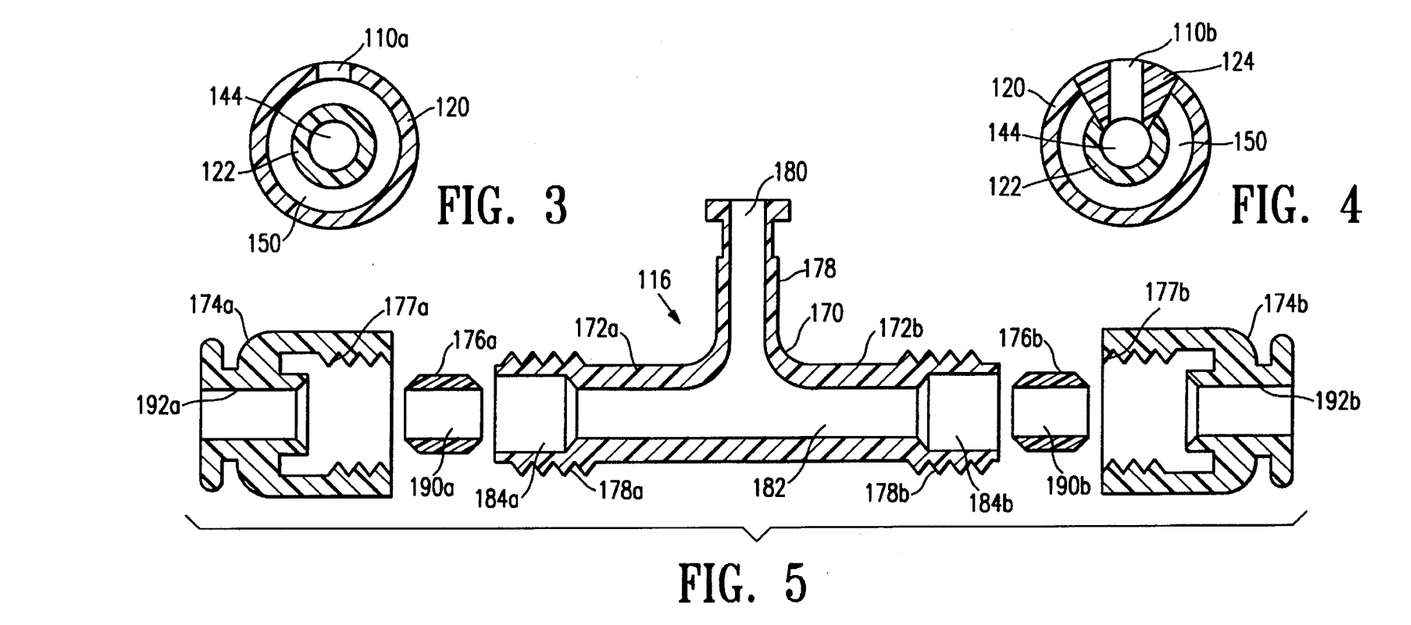
FIG. 3 is a cross-sectional view of the catheter central portion of FIG. 2 taken along line 3—3.
FIG. 4 is a cross-sectional view of the catheter central portion of FIG. 2 taken along line 4—4.
FIG. 5 is a cross-sectional view of an exemplary inflation assembly of the present invention.

As further shown in the FIGS. 2–4, central catheter body 102 defines two passages for the delivery of inflation media to respective distal bodies 104a, 104b. For instance, the passage for delivery of inflation media to dilatation balloon 106a is defined by inflation port 110b and the lumen 144 of inner hypotube 122 in fluid conducting communication with the distal lumen 146a of first distal catheter body 104a. The end of inner hypotube lumen 144 is sealed at 148 by soldering, welding, or laser-welding to prevent inflation media from escaping into the distal lumen 146a of the second distal catheter body 104b. Similarly, the passage for delivery of inflation media to dilatation balloon 106b is defined by inflation port 110a and lumen 150 of outer hypotube 120 which is in fluid conducting communication with second distal catheter body 104b. The end of lumen 150 is sealed at connection 128 in the manner described above to prevent inflation media from escaping into the lumen of first distal catheter body 104a.

Exemplary inflation assembly 116, shown more clearly in FIG. 5, is adapted for use with the embodiments of the present invention for preferentially delivering inflation media to either inflation port 110a or 110b. Exemplary inflation assembly 116 includes a central Y-connector 170 having two threaded ends 172a and 172b, with a tightening mechanism secured to each end 172a and 172b. Each exemplary tightening mechanism includes a threaded compression fitting 174a, 174b and an O-ring or grommet 176a, 176b. Those skilled in the art will appreciate that alternative Y-connectors having different features, angular configurations and tightening mechanisms may be substituted within the scope of the present invention.

More specifically, exemplary Y-connector 170 comprises an inflation arm 178 having an internal passage 180 which communicates with a bi-directional inflation channel 182. O-rings or grommets 176a, 176b have openings 190a, 190b, and compression fittings 174a, 174b are provided with channels 192a, 192b. Each end 172a and 172b has an opening 184a, 184b, respectively, which is adapted to receive O-rings or grommets 176a, 176b. Compression fittings 174a, 174b are provided with internal threads 177a, 177b which may be threadably engaged with threads 178a, 178b at both ends 172a, 172b of Y-connector 170. Central catheter body portion 102 (FIG. 1) may be received within inflation channel 182 of Y-connector 170, openings 190a, 190b of O-rings or grommets 176a, 176b, and channels 192a, 192b of compression fittings 174a, 174b, so that the combined inflation assembly 116 can slide along central catheter body portion 102 as shown in FIG. 1.

In operation, compression fittings 174a, 174b are loosely secured to ends 172a, 172b of the Y-connector 170. This loose connection is achieved by minimally engaging threads 177a and 178a, and 177b and 178b, so that the O-rings or grommets 176a, 176b positioned at the ends 172a, 172b are not compressed, thereby maintaining openings 190a and 190b at a wider diameter. This allows inflation assembly 116 to slide freely in both directions along central catheter body portion 102 to be positioned at a particular location.

When the desired location has been reached, such as where the inflation channel 182 is positioned over inflation port 110a or 110b, compression fittings 174a, 174b are tightened by turning to further engage threads 177a and 178a, and 177b and 178b. This tightening compresses O-rings or grommets 176a, 176b so that they tightly grip the catheter body 102 disposed within. This secures the inflation assembly 116 at that particular location so that an inflation media can be injected through the internal passage 180 and inflation channel 182 into the selected inflation port 110a or 110b. When inflation assembly 116 needs to be moved to another location, compression fittings 174a, 174b are loosened and the inflation assembly 116 slidingly advanced to the desired location and secured as previously described.

FIGS. 1–2 also show barbed releasable connecting members 108a, 108b near the distal ends of central catheter body portion 102. Specifically, barbed connecting member 108a is, in effect, an extension of the wall of inner hypotube 122 while barbed connecting member 108b is an extension the wall of outer hypotube 120. While barbed connecting members 108a, 108b are represented as an integral extension of the walls of inner hypotube 122 and outer hypotube 120 respectively, it is contemplated that barbed connecting members 108a, 108b may be fabricated as a separate piece and affixed to inner hypotube 122 and outer hypotube 120 through welding, adhesives or other techniques known in the art.

In either case, barbed connecting members 108a, 108b include connecting ends 64a, 64b defining barb apertures 62a, 62b at the distal ends of inner hypotube 122 and outer hypotube 120, respectively. Displaced proximally with respect to connecting ends 64a, 64b are distal barbs 66a, 66b and displaced proximally from distal barbs 66a, 66b are proximal barbs 68a, 68b. An exemplary distance from the apex of distal barb 66a to the apex of proximal barb 68a is approximately 0.13 in. Both barbs are on the exteriors of inner hypotube 122 and outer hypotube 120 and are radially oriented with respect to the central bores defined by each hypotube. Preferably, proximal barbs 68a, 68b have a slightly greater radius than distal barbs 66a, 66b. Although the illustrated embodiment incorporates two barbs on each hypotube, those skilled in the art will appreciate that other barbed configurations may work equally well and are contemplated as being within the scope of the invention.

With this understanding of the central portion of catheter 100, the distal end portions or bodies 104a, 104b are generally made of flexible polymeric materials such as polyvinylchlorides, polyethylenes, polyolefins, fluoropolymers, polyamides, polyesters, polyimides or polypropylenes. For example, a 70/30 polyethylene tubing (employing 70% high density polyethylene and 30% low density polyethylene) can be used to provide cost efficient, relatively flexible distal bodies. Those skilled in the art will appreciate that radiopaque markers may be placed anywhere along the length of the distal bodies in order to facilitate tracking in the patient.

To the distal ends of distal bodies 104a, 104b are bonded expansible dilatation balloons 106a, 106b. Slits 38a, 38b (FIG. 1) may be formed in the walls of distal bodies 104a, 104b proximal to expansible dilatation balloons 106a, 106b. In the exemplary embodiments guide tubes 40a, 40b (FIG. 2) extend through distal bodies 104a, 104b and may be somewhat stiffer than distal bodies 104a, 104b, being made for example of 100% high density polyethylene tubing. Guide tubes 40a, 40b extend proximally through the proximal ends of dilatation balloons 106a, 106b and through distal bodies 104a, 104b to slits 38a, 38b. Slits 38a, 38b define guide wire ports 112a, 112b in the wall of distal bodies 104a, 104b. The proximal open ends of guide tubes 40a, 40b are sealed to guide wire ports 112a, 112b. In other rapid exchange embodiments of the present invention, it is contemplated that guide wire ports may be positioned on central catheter body portion 102 in communication with the guide tubes.

From the foregoing discussion, those skilled in the art will appreciate that in this exemplary embodiment disposable distal bodies 104a, 104b are generally equivalent in terms of configuration. Accordingly, the remaining discussion with respect to FIGS. 1–4 will be directed to the first distal body 104a and its associated interactions with central catheter body portion 102 with the understanding that second distal body 104b operates in essentially the same manner. Exemplary differences between the two distal bodies or differences in their operation will be specifically noted.

Distal lumen 146a (FIG. 2), defined by distal tube wall 70a, terminates to form distal tube opening 74a having approximately the same internal radius as inner hypotube 122. Optional reinforcing sleeve 72a (FIG. 1) is affixed through adhesives or other conventional means to the outer surface of distal tube wall 70a along the proximal portion of the disposable distal body 104a. It must be emphasized that the present invention may be practiced without reinforcing sleeve 72a. However, when used, reinforcing sleeve 72a is preferably fabricated of a material that is somewhat stiffer than the material used to form distal tube wall 70a. In the embodiment shown, slit 38a and corresponding guide wire port 112a are positioned so as to pass through distal tube wall 70a. Alternatively, the positioning of the guide wire port 112a through optional reinforcing sleeve 72a provides added strain relief helping disposable distal body 104a retain the proper configuration during use.

Distal body 104a, which may be disposable, is easily attached to inner hypotube 122 of central catheter body portion 102 over barbed releasable connecting member 108a which is adapted to receive distal tube opening 74a. Typically, the connection is established by firmly gripping distal body 104a and aligning connecting end 64a of barb 108a with distal tube opening 74a. Distal body 104a is then advanced over barbed connecting member 108a to sealingly engage distal barb 66a and proximal barb 68a as shown in FIG. 2. Those skilled in the art will appreciate that barbs 66a and 68a on inner hypotube 122 are configured to be slightly larger in diameter than distal tube opening 74a. Similarly, barbs 66b and 68b on outer hypotube 120 are configured to be slightly larger than the appropriately sized distal tube opening 74b of distal body 104b. Accordingly, as distal body 104a is slid over external barbs 66a and 68b, the flexible material of distal tube wall 70a and any optional reinforcing sleeve 72a will distort and expand slightly to accommodate them. The radial compression of distal body 104a provided by the elastic memory of distal tube wall 70a and optional reinforcing sleeve 72a ensure a strong connection and tight seal.

The attachment strength provided by the use of a barbed connection according to the present invention is illustrated by the following nonlimiting example.

EXAMPLE I

Pull tests were performed to demonstrate the operability of using a barbed connector to releasably join a reusable proximal or central catheter body with a disposable distal catheter end or body. For testing purposes, a #20 gauge needle having an outer diameter of 0.035 in. and fabricated from stainless steel was used as a hypotube and machined to correspond to the barbed configuration shown in FIGS. 1 and 2. Accordingly, for the purposes of explanation the reference numbers of FIGS. 1 and 2 (absent the designation a or b) will be used in this Example. Distal barb 66 had a diameter of approximately 0.032 in. and was 0.169 in. from connecting end 64 while proximal barb 68 had a diameter of approximately 0,035 in. and was 0,299 in. from connecting end 64 of the hypotube of central catheter body 102.

Disposable distal body 104 was fabricated from 70/30 polyethylene and was not reinforced. The inner diameter of distal tube wall 70 was slightly smaller than the diameters of external barbs 66, 68 measuring approximately 0,029 in. The overall length of disposable distal body 104 used in the Example was approximately 2 in. Following fabrication and sizing, disposable distal body 104 was rinsed with water and dried prior to testing.

Disposable distal body 104 was first clamped with hemostats to seal it at one end. Using grips or hemostats, barbed connecting member 108 of central catheter body 102 was aligned with the non-clamped end of distal body 104 and force was applied to slide the tubing over distal barb 66 and proximal barb 68 thereby sealingly engaging distal body 104 and the hypotube of central catheter body 102. The force required to effect this engagement was easily provided by the technician without the use of additional tools. After the pieces were securely fastened, the assembly was placed in a standard pull test apparatus and secured.

Several assemblies, clamped in this manner, were subjected to pressure in the form of air applied through a tube in communication with the hypotube. Pressures of 0, 4, 8, 12, 16 and 20 atmospheres were applied to different clamped assemblies. Under these various pressures, which were held constant in each individual test, the connected distal body 104 and hypotube of central catheter body 102 were pulled apart at a constant rate of 20 in./min until some part of the assembly failed. The amount of stress or load on the assembly at the point of failure was monitored.

In each test, distal body 104 failed structurally or leaked before the barbed connection failed. That is, in each of the assemblies tested under different pressure, the seal provided by barbed connecting member 108 and distal tube wall 70 was not disrupted before material failure of distal body 104. As expected, the amount of stress necessary to effect the rupture of distal body 104 decreased as the internal air pressure was increased, yet the connection between the central catheter body portion and the distal bodies was uncompromised by the applied pressures. Those skilled in the art will appreciate that these results demonstrate that this exemplary barbed connector, or its equivalent, can easily withstand the stresses imposed by the typical inflation pressures used in dilatation catheters.

As evidenced by the data above, a strong connection may be made in accordance with the teachings of the present invention. However, when an optional reinforcing sleeve is affixed to the disposable distal body, it performs a number of different functions. For example, the reinforcing sleeve increases the strength of the distal body to ensure that it will seal tightly over the barbs. Moreover, the optional reinforcing sleeve provides strain relief to ease the transition from the semi-rigid inner hypotube to the flexible distal body. Finally, an optional reinforcing sleeve strengthens the disposable distal body in the area of the guide wire port, thereby reducing the chance of kinking the distal body upon use.

Figure 6:
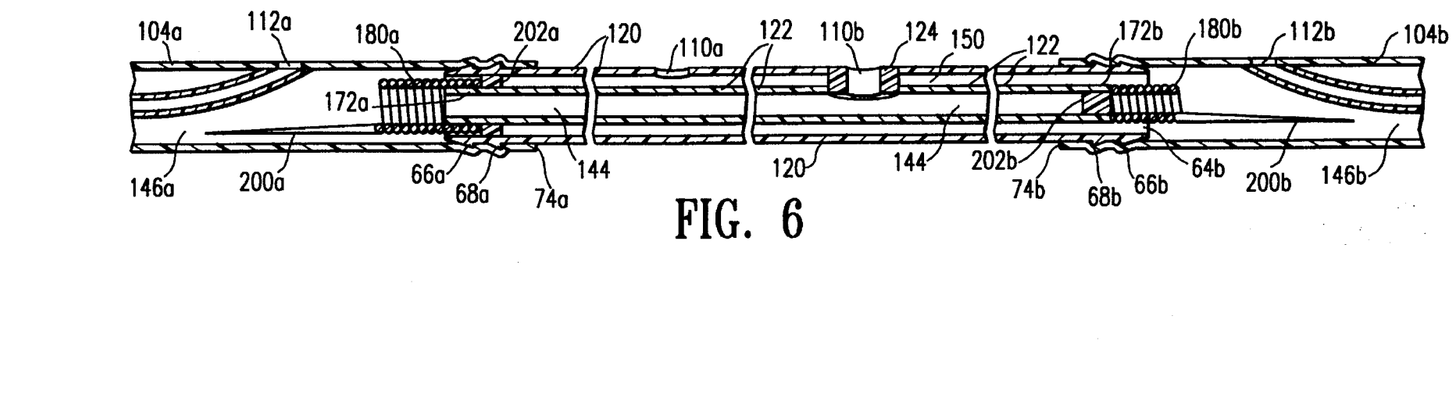
FIG. 6 is a fragmentary view of an alternative central body portion.
Figure 7:
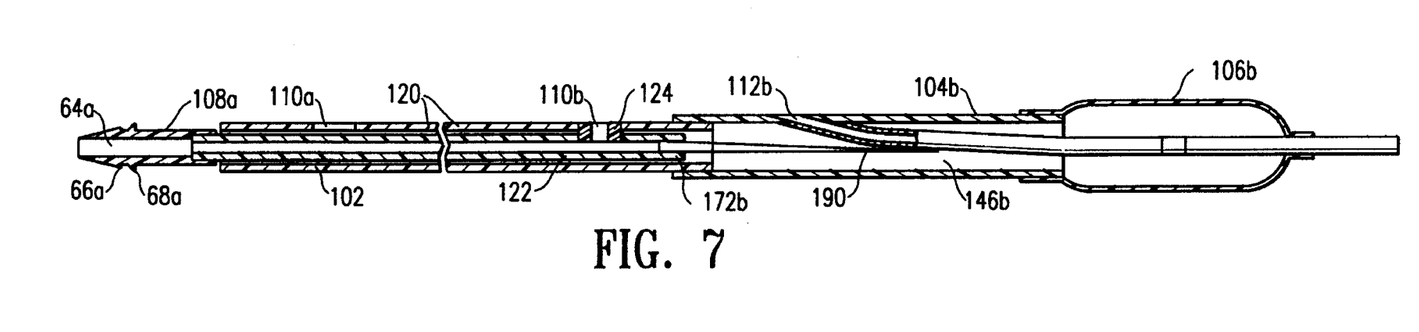
FIG. 7 is a fragmentary cross-sectional view of an alternative embodiment of the present invention.

In addition to the optional reinforcing sleeve, other reinforcing mechanisms which are compatible with the present invention are shown in FIGS. 6 and 7 where a rigid extension is used to reduce the chances of the disposable distal bodies kinking during use. Specifically, a first helical coil 180a is connected to a first end 172a of the inner hypotube 122 at radial connection 202a by soldering, welding, laser welding or other conventional means. Helical coil 180a is attached to inner hypotube 122, outer hypotube 120 or both so as not to obstruct inner hypotube lumen 144. Tapered so that it extends into distal lumen 146a of disposable distal body 104a to a location distal of the guidewire port 112a, helical coil 180a may be formed by coiling a wire, and leaving one elongate end 200a of the wire uncoiled. As with hypotubes 120, 122, the wire of helical coil 180a may be made from metal alloys such as stainless steel or Nitinol and may be used with or without an optional external reinforcement sleeve (not shown).

Similarly, a second helical coil 180b is connected to the distal end 172b of inner hypotube 122. In this case helical coil 180b is attached to inner hypotube 122 so as not to obstruct outer hypotube lumen 150. The uncoiled and tapered elongate end 200b of helical coil 180b extends into distal lumen 146b of distal catheter body 104b to a location distal of the guidewire port 112b, and operates to prevent kinking upon insertion of the catheter assembly into the patient.

FIG. 7 illustrates an alternative construction for reducing the possibility of catheter kinking. The structure and configuration of central catheter body portion 102 and disposable distal bodies 104a, 104b are substantially as discussed. However, instead of an external sleeve or a helical coil the ends of inner hypotube 122 are provided with a tapered wire 190 extending into the distal body. Specifically, tapered wire 190 is brazed or connected to end 172b of inner hypotube 122 and extends distally with respect to guidewire port 112b. It is important to note that tapered wire 190 does not obstruct fluid conducting communication between inner hypotube lumen 150 (FIG. 3) and distal lumen 146b.

Of equal importance, FIG. 7 illustrates an alternative embodiment of the present invention where only one distal body is removable and the other, distal body 104b, is fixed to the central body portion 102. As shown, central body portion 102 is provided with a releasable barbed connection 108a attached to inner hypotube 122. Thus, a variety of removable distal body portions may be attached to alter the configuration of the apparatus or to replace portions as needed. Conversely, distal body portion 104b is permanently affixed to outer hypotube 120 of central body portion 102, providing a known, standard configuration.

Coding schemes, in the form of stripes, bands, markings, characters, colors or symbols, may be used to distinguish different types, configurations or sizes of disposable distal bodies from one another. The coded distal bodies are then easily identified and selected in the operating environment by type, size, balloon configuration or any other criteria. It will, of course, be recognized that similar coding schemes may be used to readily identify the reusable catheter components as well as the disposable components.

The markings or colors used to specify the desired features may be placed in any visible location on the disposable distal body. Moreover, several different features of a particular coded distal body can be specified by using a different type of coding scheme for each feature. For example, different colors may be used to easily identify the length of the dilatation balloon. Similarly, the diameter may be denoted by the number or thickness of coding bands imprinted on the distal body. Of course, those skilled in the art will appreciate that any distinguishing feature or features of the disposable distal bodies or reusable catheter body may be communicated using various coding schemes such as those described above.

Figure 8:
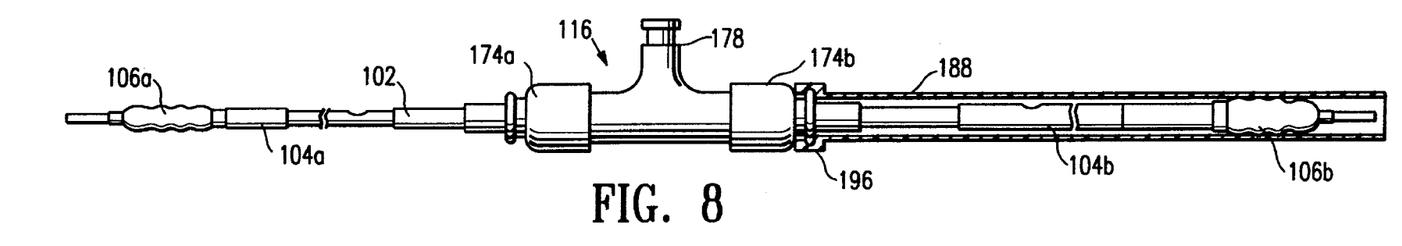
FIG. 8 is a fragmentary partial cross-section of an additional alternative embodiment of the present invention.
Figure 9:
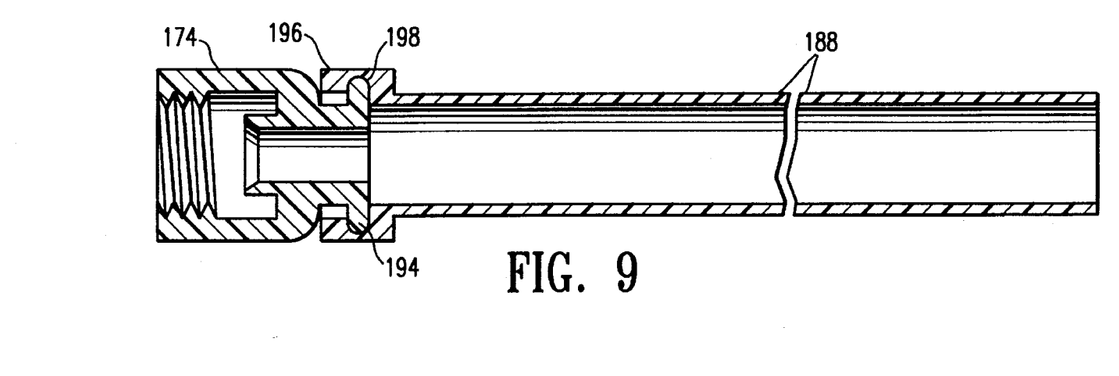
FIG. 9 is an enlarged fragmentary cross-section of an exemplary protective sheath of the present invention.

FIGS. 8 and 9 illustrate an optional protective sheath 188 which may be fitted over the unused portion of the catheter including second distal catheter body 104b. Protective sheath 188, typically formed of flexible plastic, covers the portion of the catheter that is not being used initially to protect it from damage and ensure sterility. As shown in FIG. 9, each compression fitting 174a, 174b (FIG. 5) can be provided with a flange 194 that extends radially outward. Protective sheath 188 is provided with a corresponding receiving end 196 having a radial well 198 adapted to receive and engage flange 194. This engagement secures and immobilizes protective sheath 188 during use of the opposite end of the device.

In addition to protecting the unused distal end, sheath 188 provides an added degree of rigidity and control to facilitate manipulation of the entire device. Then, if necessary, a simple tug of sheath 188 will disengage receiving end 196 from flange 194, uncovering the unused distal body portion for immediate use.

With this understanding of the structural features of these exemplary embodiments of the present invention, their use can be understood as follows. Prior to performing surgery, the dual headed catheters of the present invention are removed from any packaging and prepped for use. In some instances the entire catheter, with two dilatation balloons attached, may be preassembled and removed from sterile factory packaging ready for use. Alternatively, the disposable distal bodies will be removed from their packaging and affixed to the reusable central catheter body under aseptic conditions at the site of the surgery. In such cases the disposable distal bodies are preferably coded to provide easy identification and allow rapid selection of the desired configuration. For example, in FIG. 1 central catheter body portion 102 may have been autoclaved or otherwise sterilized at the hospital. In this case, disposable distal tubular bodies 104a, 104b would be removed from sterile packaging and connected with central catheter body portion 102 in the operating area. The catheter may be assembled simply by hand or by using tools especially adapted for the task and included in the packaging.

During use of the catheter configurations discussed above, a guide wire is first positioned across the stenosis. An optional protective layer is removed from inflation port 110b and inflation assembly 116 is then advanced along central catheter body 102 so that it is positioned over inflation port 110b. Compression fittings 174a, 174b of inflation assembly 116 are then tightened to secure inflation assembly 116 in place over inflation port 110b. After first distal body 104a has been primed to displace any air, it is inserted into the artery by positioning the proximal end of the guidewire 114 within the distal opening of body portion 104a so that the proximal end of the guidewire traverses guide tube 40a and exits guidewire port 112a. The collapsed dilatation balloon 106a continues to advance along the guide wire inside the patient until it reaches the treatment area where its motion is stopped.

Inflation media is introduced through internal passage 180 (FIG. 5), passing through inflation channel 182 of the inflation assembly 116 and through inflation port 110b before entering lumen 144 (FIG. 2) of inner hypotube 122. The inflation media then passes through distal lumen 146a (FIG. 2) of first disposable distal body 104a and inflates dilatation balloon 106a to dilate or redistribute the stenosis. Dilatation balloon 106a is then deflated and withdrawn from the artery while maintaining the guidewire 114a in the same position for guide wire reaccess.

Depending upon the circumstances and needs of the operating physician, for example if dilatation is unsuccessful, first disposable distal body 104a can be removed from catheter body 102 and replaced with a new, sterile distal body or, more simply, the dual headed catheter can be reversed and second disposable distal body 104b can be inserted into the patient. Assuming that distal body 104b has been properly selected beforehand and meets the immediate requirements of the physician, this second option would be preferred as it saves time and simplifies the procedure.

As discussed above, it is possible to provide both the first and second distal catheter bodies 104a and 104b with balloons of different lengths, diameters, and materials. The need for different size balloons is the most typical reason for exchanging or replacing a catheter. Different diameters produce different deflation times depending on balloon size. It is also possible to provide both first and second distal bodies 104a and 104b having different distal body lengths.

If second distal body 104b is to be used, optional protective sheath 188 is removed and any protective layer removed from inflation port 110a. Compression fittings 174a, 174b are loosened so that inflation assembly 116 can be moved from its position over inflation port 110b and advanced along central catheter body 102 to a position over inflation port 110a. Compression fittings 174a, 174b of inflation assembly 116 are then tightened to secure it in place over inflation port 110a. After second distal catheter body 104b has been primed, catheter assembly 100 is then reversed so that second distal catheter body 104b can be inserted into the artery by positioning the proximal end of guidewire 114a through the distal opening of distal body 104b so that the proximal end of guidewire 114a traverses guide tube 40b and exits guidewire port 112b.

Second distal catheter body 104b is then advanced along the artery to the location of the stenosis. Inflation media is introduced to lumen 150 of outer hypotube 120 through inflation assembly 116 and inflation port 110a. The inflation media passes through lumen 150, distal lumen 146b of the second distal catheter body 104b inflating dilatation balloon 106b to dilate or redistribute the stenosis. At the end of this procedure, the second distal catheter body 104b may be withdrawn. If desired, alternative or additional distal bodies may be affixed to central catheter body portion 102 and the process repeated utilizing the releasable connectors as discussed above.

Following completion of the procedure, the catheter assembly is removed from the patient and taken apart using normal procedures for handling biologically contaminated instruments. For example, distal bodies 104a, 104b can be detached by hand or with tools and discarded. However, in direct contrast to prior art dilatation catheters, reusable central catheter body portion 102 can be cleaned and resterilized. Initially, catheter body 102 may be soaked in alcohol or other disinfectants to reduce the possibility of inadvertent disease transmission. After the initial soaking, catheter body 102 may be purged and cleaned using fluids, preferably disinfectants, injected through inflation ports 110a, 110b. This reusability substantially reduces the expense and the amount of medical waste generated by the procedure.

Once the reusable central portion of the catheter has been cleaned, it may be placed in an autoclave pouch or other appropriate packaging and resterilized. Those skilled in the art will appreciate that any technique commonly used to sterilize medical instruments can be used in connection with the reusable portions of the catheters of the present invention. For example, reusable central portion 102 may be sterilized using irradiation, heat, autoclaving or by exposure to liquid or gaseous disinfectants. When sterile, the reusable portion may be stored under aseptic conditions until another disposable distal body is attached and the catheter prepped for use.

Figure 10:
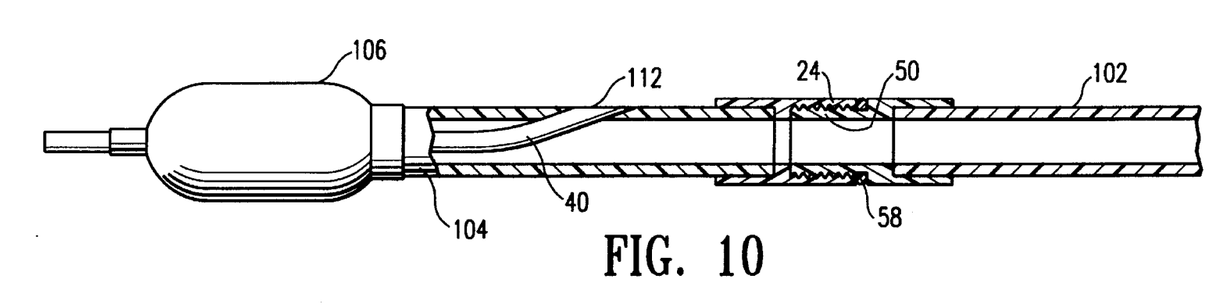
FIG. 10 is an enlarged partial cross-section of an alternative releasable connector of the present invention.

An alternative dual headed reusable rapid exchange catheter embodiment is shown in FIG. 10. In this embodiment, central catheter body portion 102 and the balloon assembly on distal bodies 104a, 104b are essentially the same as those previously discussed. However, in the embodiment shown in FIG. 10, an alternative releasable connection is used to join central catheter body portion 102 with disposable distal bodies 104a, 104b. Unlike the previously described embodiments which incorporate barbed connecting members 108a, 108b, the embodiment shown in FIG. 10 uses a threaded connection including male connecting member 50 and female connecting member 24 to attach the disposable distal body 104 to the central body portion 102.

As with the previous embodiments, the catheter shown in FIG. 10 includes a reusable elongate central catheter body portion 102 and at least one disposable distal body 104. Dilatation balloon 106, guide tube 40 and guidewire port 112 are further provided. Inflation assembly 116 can be slidably positioned on central catheter body portion 102 as described above.

Male connecting member 50 is positioned at the distal end of inner hypotube 122 or outer hypotube 120 as desired. Preferably constructed of a relatively rigid material, male connecting member 50 may be bonded or welded into place. Alternatively, male connecting member 50 may be machined directly from the hypotube.

At the proximal end of disposable distal body 104, female connecting member 24 is affixed using adhesives or other common bonding techniques. Preferably fabricated from a relatively rigid polymeric material, female connecting member 24 defines the aperture at the proximal end of disposable distal body 104. Threads are positioned on the exterior surface of the proximal end of male connecting member 50 which is further provided with a gasket or O-ring 58. O-ring 58 is urged into sealing engagement upon attachment of male connecting member 50 to female connecting member 24. Gasket 58 may be made of silicone or other pliant polymeric materials and has an exemplary inner diameter of 0.028 in.

In combination, both connecting members 24 and 50 exhibit a low profile and do not substantially increase the absolute diameter of the catheter assembly.

Tightening female connecting member 24 urges gasket 58 into sealing engagement. When central catheter body portion 102 is connected with disposable distal body 104, fluid conducting communication is established longitudinally through the catheter assembly allowing inflation of expansible balloon 106 through the injection of inflation media as described previously.

The rapid exchange reusable dual headed catheter assembly illustrated in FIG. 10 is used in substantially the same way as the earlier described embodiments. Disposable distal bodies 104a, 104b and reusable central catheter body portion 102 may be supplied separately or in a preassembled state for immediate use. Of course, the disposable distal ends may be substantially equivalent or differ in terms of balloon size, length, texture or other functional characteristics. During the procedure, one of the two dilatation balloons 106a, 106b is advanced into position across the stenosis using a preinserted guidewire 114a. Following use, the disposable distal end is withdrawn from the patient. If necessary, at this point the surgeon may insert the second distal end or, if desired, replace the first distal end and insert the newly fitted replacement balloon in the patient over the previously inserted guidewire. Following completion of the procedure and removal of the assembly, the catheter may be disassembled and the reusable components resterilized and stored under aseptic conditions for later use.

Figure 11:
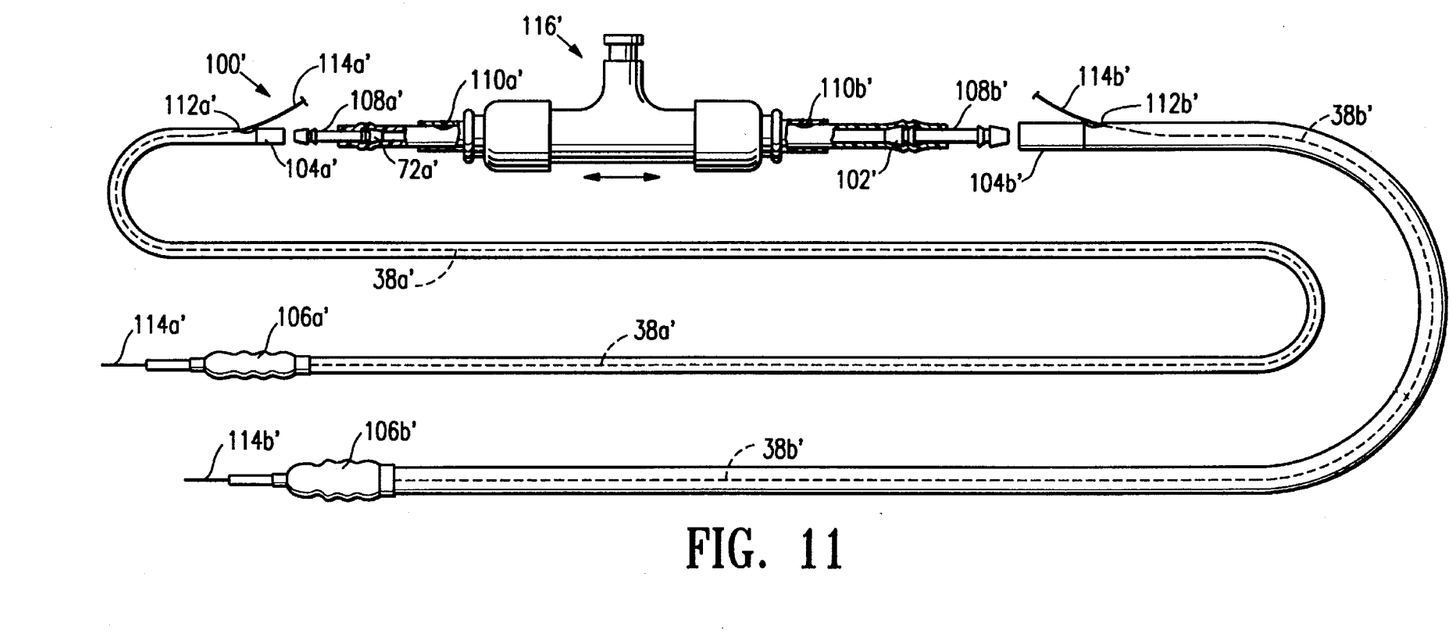
FIG. 11 is a partial fragmentary view of an additional alternative embodiment of the present invention.

FIG. 11 illustrates an alternative embodiment of the present invention wherein double-male barbed connectors 108a' and 108b' connect central catheter body 102' to distal bodies 104a' and 104b', respectively In this embodiment the double-male barbed connectors 108a' and 108b' may be disposable.

The principles of the present invention are broad-based and with minimal modification may be applied to all the currently-available types of catheter systems including "rapid-exchange" "over-the-wire" and "fixed-wire" systems. The double balloon catheter assemblies of the present invention provide two easy-to-use catheter systems on the same catheter assembly. This allows angioplasty and catheter exchange to be performed economically, quickly, and conveniently while retaining all the necessary safety precautions. The resultant economic savings are not insignificant in light of the current demand for lower health care costs, and can be realized from several aspects: the reduced cost of providing one catheter assembly instead of two separate catheters; fewer disposable materials; and less inventory and lower administrative costs for the hospitals.

In closing it is to be understood that the embodiments of the invention disclosed herein are illustrative of the principles of the invention and that other modifications may be employed which are within the scope thereof. It is not necessary that both distal ends of the catheter assembly be replaceable or operate under the same principles. For example, one distal catheter body may provided and configured to operate as an "over-the-wire" catheter while the other may be configured to operate as a "rapid-exchange" catheter or as a "fixed-wire" catheter. Thus, any combination of the various "fixed wire" "over-the-wire" and "rapid-exchange" principles may be employed on a single catheter assembly without departing from the spirit and scope of the present invention.

Those skilled in the art will further appreciate that the present invention may be embodied in other specific forms without departing from the spirit or central attributes thereof. In that the foregoing description of the present invention discloses only exemplary embodiments thereof, it is to be understood that other variations are recognized as being within the scope of the present invention. Accordingly, the present invention is not limited to the particular embodiments which have been described in detail herein.

What is claimed is:

1. A dual headed catheter assembly comprising:

a generally tubular elongate central body having generally opposed first and second ends and at least one lumen extending therethrough;

a first elongate tubular distal body having proximal and distal ends, an inflatable member with an inner chamber near the distal end a first longitudinally extending bore in communication with said lumen in said central body and the interior of the inflatable member and being releasable and sealingly connected at its proximal end to said first end of said central body portion;

a second elongate tubular distal body having proximal and distal end and being sealingly connected at its proximal end to said second end of said central body and provided with a second longitudinally extending bore in communication with said lumen in said central body; and means associated with the central body to selectively engage in fluid communication either the first or second longitudinally extending bore with a source of fluid.

2. The dual headed catheter assembly of claim 1 including a connector member to releasably connect the proximal end of the first elongate tubular distal body to the central body.

3. The dual headed catheter assembly of claim 1 including a connector member to releasably connect the proximal end of the second elongate tubular distal body to the central body.

4. The dual headed catheter assembly of claim 3 further comprising a second releasable connector disposed between said second end of said central body and said proximal end of said second elongate tubular distal body.

5. The dual headed catheter assembly of claim 1 wherein said first elongate tubular distal body is provided with an expansible balloon disposed adjacent the distal end thereof which has an interior in fluid communication with the longitudinally extending bore thereof.

6. The dual headed catheter assembly of claim 5 wherein said central body is provided with a first inflation port in fluid communication with said lumen thereof and said longitudinally extending bore of said first tubular distal body.

7. The dual headed catheter assembly of claim 6 wherein, said second elongate tubular distal body is provided with a second expansible balloon disposed adjacent the distal end thereof and said central body is provided with a second inflation port and a second inflation lumen in fluid communication between said second inflation port and said second expansible balloon.

8. The dual headed catheter assembly of claim 7 wherein the central body is provided with means to deliver inflation fluid to either said first inflation port or said second inflation port.

9. A method for performing a medical procedure within a patient, said method comprising the steps of:

providing the dual headed catheter assembly of claim 1; and inserting at least one of said first or said second elongate tubular distal bodies into the patient.

10. The method of claim 9 further comprising the additional steps of disconnecting said first elongate tubular body from said first end of said central body portion;

connecting a replacement tubular distal body to said first end of said central body portion; and inserting at least one of said second elongate tubular distal body or said replacement tubular distal body into the patient.

11. A dual headed catheter assembly comprising:

a generally tubular elongate central body having generally longitudinally opposed first and second ends, first and second parallel lumens extending therethrough and coextensive at least in part, a first inflation port in fluid communication with said first parallel lumen and a second inflation port in fluid communication with said second parallel lumen;

a first elongate tubular distal body sealingly connected at its proximal end to said first end of said central body and provided with at least one longitudinally extending bore in communication between said first parallel lumen in said central body and a first expansible balloon disposed adjacent the distal end of said first elongate tubular distal body;

a second elongate tubular distal body sealingly connected at its proximal end to said second end of said second end of said central body and provided with at least one longitudinally extending bore in communication between said second parallel lumen in said central body;

a releasable connector disposed between said first end of said central body and said proximal send of said first elongate tubular distal body.

12. The dual headed catheter assembly of claim 11 further comprising a second releasible connector disposed between said second end of said central body portion and said proximal end of said second elongate tubular distal body.

13. The dual headed catheter assembly of claim 11 further comprising a protective sheath for releasably covering one of the first or second tubular distal bodies while the other tubular distal body is in use.

14. The dual headed catheter assembly of claim 11 wherein said first elongate tubular distal body is provided with a guide wire lumen disposed along at least a portion of its longitudinal extent and said second elongate tubular distal body is provided with a guide wire lumen disposed along at least a portion of its longitudinal extent.

15. The dual headed catheter assembly of claim 11 wherein said first and second parallel lumens are coaxially disposed with respect to one another.

16. The dual headed catheter assembly of claim 11 wherein the central body is provided with means to deliver inflation fluid to either said first inflation port or said second inflation port.

17. The dual headed catheter assembly of claim 16 wherein said inflation assembly comprises a fluid conducting generally tubular body sealingly disposed about said central body portion in adjustable sliding relationship between a first position in fluid conducting communication with said first inflation port and a second position in fluid conducting communication with said second inflation port.

18. A method for performing an angioplasty procedure to dilate a vascular stenosis within a patient, said method comprising the steps of:

providing the dual headed catheter assembly of claim 7;

inserting said first elongate tubular distal body into the patient and advancing said first expansible balloon to a position crossing the stenosis;

inflating said first expansible balloon;

deflating said first expansible balloon and withdrawing said first elongate tubular distal body from the patient;

inserting said second elongate tubular distal body into the patient and advancing said second expansible balloon into a position across the stenosis; and deflating said second expansible balloon and withdrawing said second elongate tubular distal body from the patient.

19. The method of claim 18 further comprising the additional steps of disconnecting said first elongate tubular distal body from said first end of said central body portion following withdrawal of said first elongate tubular distal body from the patient;

connecting a replacement tubular distal body to said first end of said central body portion; and inserting said replacement tubular distal body into the patient.

20. The method of claim 19 further comprising the additional steps of removing said replacement tubular distal body from the patient;

disconnecting said replacement tubular distal body from said first end of said central body portion;

connecting an alternative replacement tubular distal body to said first end of said central body portion; and inserting said alternative replacement tubular distal body into the patient.

21. A catheter assembly comprising:

a) an elongated body which includes a central section having first and second ends, a first inflation lumen extending to the first end, a second inflation lumen extending to the second end, a first port in fluid communication with the first inflation lumen, and a second port in fluid communication with the second inflation lumen, a first extremity releasably connected to the first end of the central section and having a third inflation lumen extending therein in fluid communication with the first inflation lumen, a first balloon on the first extremity having an interior in fluid communication with the third inflation lumen, a second extremity connected to the second end of the central section and having a fourth inflation lumen extending therein in fluid communication with the second inflation lumen, a second balloon on the second extremity having an interior in fluid communication with the fourth inflation lumen; and b) a connector element having first and second ends, a first inner lumen which is configured to slidably receive the central section of the elongated body, means on the first and second ends of the connector element to sealingly engage a first portion of the central section of the elongated body on one side of one of the inflation ports in the central section and a second portion of the central section of the elongated body on the opposite side of said one of the inflation ports to selectively engage in fluid communication either the first or the second inflation lumens and a second inner lumen having one end in communication with the first inner lumen and a second end configured to be connected to a source of inflation fluid.

22. The catheter assembly of claim 21 wherein the second balloon has a larger inflated diameter than the inflated diameter of the first balloon.

23. The catheter assembly of claim 21 wherein the central section comprises an outer tubular member and an inner tubular member disposed within the outer tubular member.

24. The catheter assembly of claim 23 wherein at least one of the inner and outer tubular members is formed of hypo-tubing.

25. The catheter assembly of claim 23 wherein the second inflation lumen is defined between the inner tubular member and the outer tubular member.

26. The catheter assembly of claim 23 wherein the second inflation port extends through a wall portion of the outer tubular member and is in fluid communication with the second inflation lumen.

27. The catheter assembly of claim 23 wherein the inner tubular member defines the first inflation lumen.

28. The catheter assembly of claim 23 wherein the first inflation port extends through a wall portion of the outer tubular member and a wall portion of the inner tubular member and is in fluid communication only with the first inflation lumen.

29. The catheter assembly of claim 23 wherein the catheter shaft of the first extremity has a distal end, a first guidewire port in the distal end, a second guidewire port spaced proximally from the balloon on the first extremity and a guidewire passageway extending from the first guidewire port to the second guidewire port.

30. The catheter assembly of claim 29 wherein the guidewire passage is defined by an inner tubular sleeve disposed within the catheter shaft of the first extremity.

31. The catheter assembly of claim 29 wherein the catheter shaft of the second extremity has a distal end, a third guidewire port in the distal end, a fourth guidewire port spaced proximally from the balloon on the second extremity and a second guidewire passageway extending from the third guidewire port to the fourth guidewire port.

32. The catheter assembly of claim 31 wherein the second guidewire passage is defined by an inner tubular sleeve disposed within the catheter shaft of the second extremity.

* * * * *